United States Patent [19]

Burroughs

[11] 4,303,241
[45] Dec. 1, 1981

[54] SPORTS VISION TRAINING DEVICE

[76] Inventor: Wayne A. Burroughs, 630 Arnold La., Winter Springs, Fla. 32708

[21] Appl. No.: 177,116

[22] Filed: Aug. 11, 1980

[51] Int. Cl.³ .............................................. A63B 71/02
[52] U.S. Cl. ........................... 273/26 C; 273/DIG. 17
[58] Field of Search ................ 273/26 C, 55 R, 29 A, 273/26 R, 1 B, 411

[56] References Cited

U.S. PATENT DOCUMENTS 3,593,997 7/1971 Boehner ............................ 273/26 R
4,022,466 5/1977 Kaiser .................................. 273/1 B Primary Examiner—Richard C. Pinkham
Assistant Examiner—T. Brown
Attorney, Agent, or Firm—Duckworth, Allen, Dyer & Pettis

[57] ABSTRACT

A training device for a sports player includes a sensor for generating a timing signal when the trajectory of a ball commences from a predetermined release area. The timer receives the timing signal from the sensor and generates a delayed output signal at a predetermined time interval after the timing signal is received. A vision interrupter device is connected to the timer and positioned in the player's line of vision between the player and the location of the ball release area. The vision interrupting device interrupts the player's vision of the ball when the delayed output singal is received from the timer so that the player can observe the trajectory of the ball for only a predetermined time after it is released.

18 Claims, 6 Drawing Figures

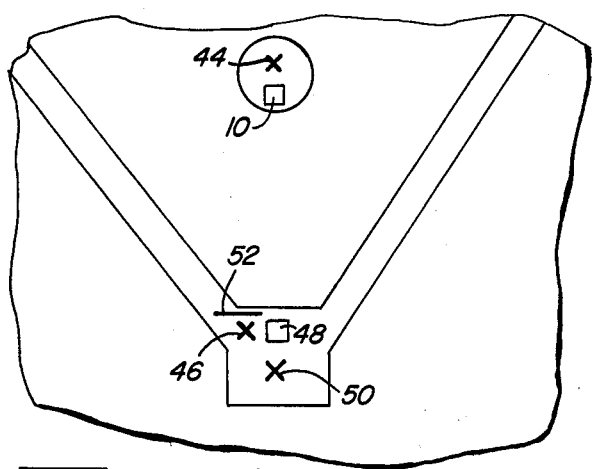
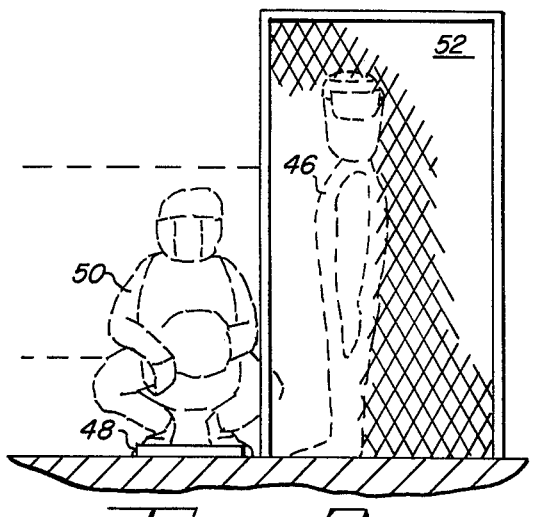
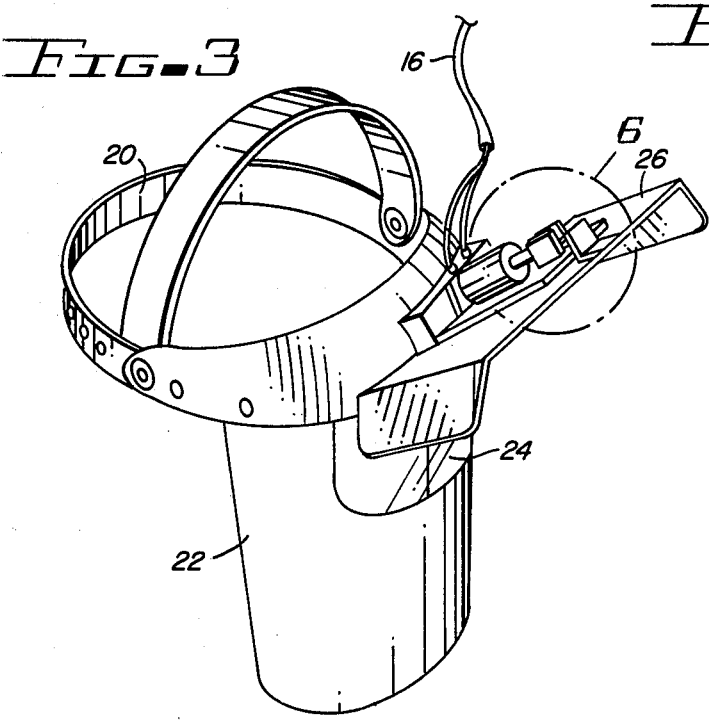
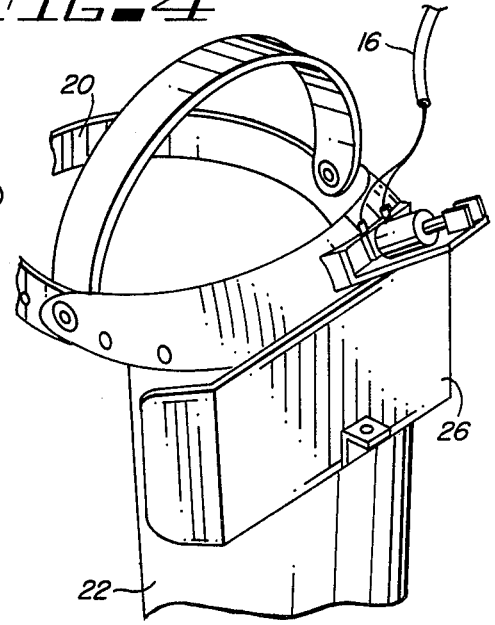
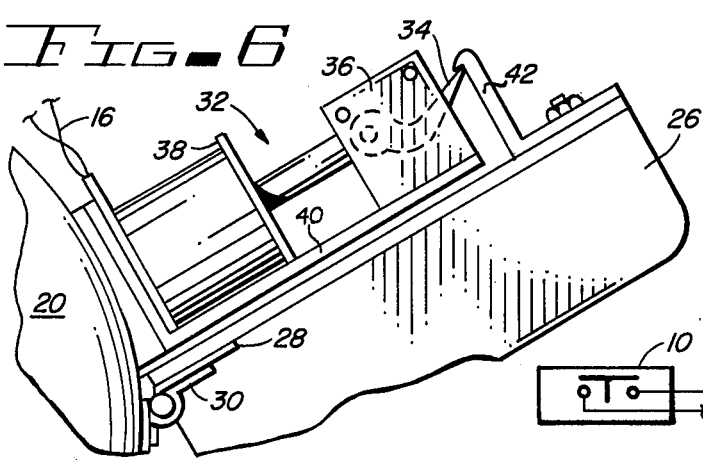
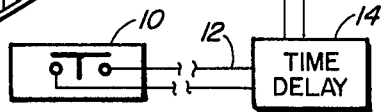

4,303,241

SPORTS VISION TRAINING DEVICE

BACKGROUND OF THE INVENTION

1. Field of the Invention

This invention relates to athletic training devices, and more particularly, to athletic vision training devices for sports activities involving a ball.

2. Description of the Prior Art

The prior art includes a number of athletic training devices, and specifically devices which are adapted to train baseball batters or baseball pitchers.

U.S. Pat. No. 3,593,997 (Boehner) discloses a baseball batting cage having enclosed top, back and side surfaces with slideable front panels which define selectable obstructed and unobstructed regions in the front portion of the cage.

SUMMARY OF THE INVENTION

It is therefore a primary objective of the present invention to provide a vision training device which permits a player to observe the trajectory of a ball, or related game projectile for only a predetermined time after it is released to train sports players to increase their ability to derive visual information from the initial trajectory of the ball or projectile.

Another object of the present invention is to provide a vision training device which can measure the quantity and accuracy of visual information perceived by a sports player from the initial trajectory of a ball or projectile.

Yet another objective of the present invention is to provide a vision training device which permits the trajectory time/distance seen by a player to be accurately controlled and varied.

Briefly stated, and in accordance with one embodiment of the invention, a vision training device for a sports player comprises sensor means for generating a timing signal when the trajectory of a ball or related projectile commences from a predetermined release area. Timing means is coupled to the sensor means to receive the timing signal and to generate a delayed output signal at a predetermined time interval after the timing signal is received. Interrupting means is coupled to the timing means and positioned in the player's line of vision between the player and the location of the ball release area to interrupt the player's view of the ball when the timing means generates the delayed output signal. The present invention permits a player to observe the trajectory of a ball for only a predetermined time/distance after it is released.

DESCRIPTION OF THE DRAWINGS

The invention is pointed out with particularity in the appended claims. However, other objects and advantages together with the operation of the invention may be better understood by reference to the following detailed description taken in connection with the following illustrations wherein:

FIG. 1 is a schematic representation indicating the relative positioning and spacing of the various elements of the present invention.

FIG. 2 indicates the relative position of the batter, catcher and home plate when the present invention is used in a baseball environment.

FIG. 3 is a perspective view from above of the vision interrupting device of the present invention, showing the visor in the latched or open position.

FIG. 4 illustrates the visor in the unlatched or closed position.

FIG. 5 is a schematic diagram illustrating the manner in which the various elements of the present invention are coupled together.

FIG. 6 is an enlarged, partially cut-away view of the latching mechanism of the present invention illustrated in FIG. 3.

DESCRIPTION OF THE PREFERRED EMBODIMENT

In order to better illustrate the advantages of the invention and its contributions to the art, a preferred hardware embodiment of the invention will now be described in some detail. In the specific preferred embodiment of the invention described below, the sports vision training device is utilized to either measure or enhance a baseball batter's perception of the initial travel of a pitched baseball immediately after a pitcher releases the ball.

Referring now to FIGS. 1 and 5, a pressure sensitive switch 10 includes a front or leading edge which is positioned approximately forty inches in front of the rubber on which the pitcher stands when winding up to pitch. Generally a thirty-two inch by forty inch pressure sensitive mat is satisfactory and the forty inch dimension is positioned parallel with a line drawn between the pitcher and the catcher. A pressure sensitive switch having these dimensions and positioned in this manner will be reliably activated at the moment the pitcher's lead foot strikes the ground. A pressure sensitive detector mat manufactured and sold by Nutone, Inc., (model No. S 2271-25) operates satisfactorily. Generally, it is advantageous to position a plywood base below pressure sensitive switch 10 and a protective covering such as a mat of artificial turf having the same dimensions as pressure sensitive switch 10 directly above switch 10. The impact of the pitcher's foot upon pressure sensitive switch 10 closes the contacts of this switch.

Pressure sensitive switch 10 is coupled by a two conductor cable 12 to an electric timer 14. In the preferred embodiment of the present invention a decade interval timer of the type manufactured by the Hunter Manufacturing Company of Iowa City, Iowa (Model 100C; series D) is utilized.

The timing signal generated by the closure of the contacts of switch 10 is coupled to the input terminals of timer 14 by cable 12 and timer 14 generates a delayed output signal after a predetermined time delay interval. In the disclosed embodiment, timer 14 generates a delayed output signal in the form of a 24 volt D.C. voltage which is coupled by cable 16 to interrupting means generally indicated by reference number 18.

FIGS. 3 and 4 illustrate that interrupting means 18 includes a helmet 20 having a plastic face shield 22. A commercially available Sears Craftsman two-part face shield/helmet assembly can be used for these elements of the present invention. The transparent Sears face shield must be painted with an opaque paint except for an aperture indicated by reference number 24 which remains transparent.

Referring now also to FIG. 6, an opaque visor 26 is coupled by a hinge 28 to helmet 20. A spring 30 is coiled around the center of hinge 28 and serves as biasing means which biases hinge 28 to the closed position and visor 26 to a position overlapping and closing off aperture 24 as illustrated in FIG. 4.

Locking means illustrated generally by reference number 32 is coupled to mounting bracket 40 and includes a latch 34 incorporated within housing 36. The latch/housing assembly is a readily obtainable commercially available unit which includes spring biasing means which biases latch 54 into the extended or locked position illustrated in FIG. 6. A 24 volt D.C. solenoid 38 is coupled to mounting bracket 40 and to latch 36. A holding clip 42 is coupled to the lower, outer surface of visor 26 as illustrated. In FIG. 6, latch 34 is illustrated in the first position. In this position latch 34 engages holding clip 42 and maintains visor 26 in the raised or open position against the downward spring biasing force exerted by spring 30 on hinge 28.

The operation and use of the present invention will now be discussed in some detail. When a pitcher throws a ball, his lead foot strikes pressure sensitive switch 10 0.06–0.10 seconds prior to his release of the baseball. The impact of the pitcher's foot on pressure sensitive switch 10 closes the switch contacts and transmits a timing signal through cable 12 to timer 14. After a predetermined time delay, timer 14 generates a 24 volt D.C. delayed output signal which is transmitted via cable 16 to solenoid 38. This D.C. voltage actuates solenoid 38, displacing latch 34 toward solenoid 38 and into a second position which releases latch 34 from holding clip 42. The biasing force exerted by spring 30 and gravitational force then very rapidly displace visor 26 from the first or open position illustrated in FIG. 3, into the closed or second position illustrated in FIG. 4. A batter or other individual wearing the interrupting means of the present invention thus very quickly has his vision of the ball interrupted.

Referring now to FIGS. 1 and 2, the general layout and positioning of the elements of the present invention will now be described. As was mentioned above, the leading edge of pressure actuated switch 10 is positioned approximately forty inches in front of the pitching rubber indicated in FIG. 1 by reference number 44. A batter indicated by reference number 46 stands in a normal batting position adjacent to home plate 48. A catcher 50 also assumes his normal catching position behind home plate 48. An open mesh protective screen 52 is positioned between the pitcher and batter 46 as illustrated in FIG. 1 to prevent the batter from being hit by wild pitches. Since the batter's vision is obstructed by the helmet/visor assembly substantially before the ball is caught by the catcher, a protective screen is strongly recommended to protect the batter from injury. In the preferred embodiment of the present invention, protective screen 52 includes an eighty inch by forty inch frame which supports chain link fence material. Protective screen 52 also includes a base which maintains it in an upright position.

While FIG. 1 illustrates the present invention as being utilized on a normal baseball playing field, the various elements of the present invention can be positioned in the general layout illustrated in FIG. 1 virtually anywhere other than a baseball playing field. Timer 14 and cables 12 and 16 are positioned at a convenient, unobtrusive location as desired.

In the baseball environment illustrated in FIG. 1, timer 14 might be set to generate a time delay of somewhere between one-tenth to two-tenths of a second. As the batter becomes more skilled in perceiving visual cues from the initial part of the trajectory of the baseball, the time delay generated by timer 14 can be shortened.

Batter 46 assumes a normal batting stance and turns his head to watch the pitcher as he normally would if he were going to attempt to hit the ball with a bat. Visor 26 is positioned in the retracted position illustrated in FIG. 3. As the pitcher releases the baseball from his hand, his lead foot strikes pressure sensitive switch 10 which transmits a timing signal to timer 14. After a predetermined time delay, timer 14 generates a delayed output signal which triggers solenoid 38, displacing latch 34 into the second or retracted position which releases latch 34 from holding clip 42. Visor 26 is very quickly displaced into a closed position and the batter's vision of the thrown baseball is virtually immediately interrupted. The catcher catches the pitched ball in a normal manner.

A specialized twenty-four square rectangular response grid has been designed for use by the batter and catcher. This imaginary rectangular response grid includes four horizontal positions and six vertical positions which permit the batter to verbally indicate the position where he perceives that the pitched ball would pass the plate based on his observation of only the initial part of the trajectory of the pitched baseball. The catcher utilizes this same imaginary response grid to accurately determine where the pitched ball actually crossed the plate. The horizontal grid position of the location where the ball crosses the plate is indicated as follows:

(1)—inside pitch (a "ball")
(2)—inside half of the plate (a "strike")
(3)—outside half of the plate (a "strike")
(4)—outside (a "ball")

The following group designations are used to indicate the vertical grid position at which the pitched ball crosses the plate:

high; (a "ball")
chest; (a "strike")
belt; (a "strike")
thighs; (a "strike")
knees; (a "strike")
low, (a "ball")

Based on his observation of only the limited portion of the trajectory of the pitched ball, the batter calls out his perceived estimate of the position at which the pitched ball crossed the plate. The batter might call out "fast ball, knees, two." This would indicate that the batter perceived that the pitcher had thrown a fast ball, vertically located at about the knee-high position, and at a lateral position indicated by the digit "2" which corresonds to the inside half of the plate in terms of lateral position. The catcher might then call out the actual measured grid positions at which the ball crossed the plate as follows: "Fast ball, thighs, 2." This would indicate that the pitched ball actually was a fast ball and that it crossed the plate at a vertical elevation corresponding to the thighs position and that it did in fact cross the inside half of the plate. In this hypothetical example, the batter's perception would be characterized as a "near-miss," indicating that the batter's perception was incorrect by only one grid position, in this case a vertical grid position. The batter's response would be characterized as incorrect if the batter announced grid positions which were wrong in both the horizontal and vertical axes by one grid square or more.

After repetitive training, it has been experimentally determined that the batter's ability to visually judge the type of pitch as well as the pitched ball's plate-crossing position can be substantially increased over time. The batter learns very quickly to concentrate on the initial trajectory of the pitched ball to determine the characteristic of the pitch as well as the horizontal and vertical grid position at which the ball will cross the plate. Batters are thereby able to increase their batting performance to a measurable degree.

The sport vision training device of the present invention is not only suitable as a training device to improve the sports player's visual accuity, but can also be utilized to measure the amount and accuracy of visual information perceived by a sports player from only the first part of a visual event, such as the initial trajectory of a pitched baseball. This measurement ability could be useful to evaluate the skill levels of less experienced baseball players or to identify a problem area for a highly experienced baseball player.

It will be apparent to those skilled in the art that the disclosed vision training device may be modified in numerous ways and may assume many embodiments other than the preferred form specifically set out and described above. For example, the vision training device of the present invention can be used with virtually any athletic activity involving a player who has to intercept a ball which is thrown, kicked, or hit toward him. For instance, the present invention could readily be adapted to be used to train players to perceive with improved accuity the trajectory of a soccer ball, a tennis ball, a hockey puck, and other related types of balls or projectiles used in various athletic events.

Sensor means in the form of a pressure sensitive switch has been disclosed in connection with the baseball version of a preferred embodiment of the invention, although optical, sound-actuated, or various other equivalent sensor means could readily be adapted to function as a sensor means for generating a timing signal when the trajectory of a ball or other game projectile commences from a predetermined release area. The interrupting means of the present invention could also take many forms other than the shutter assembly disclosed above. The interrupting means may also be positioned at a location intermediate to the player and the area from which the trajectory of the ball commences. Accordingly, it is intended by the appended claims to cover all such modifications of the invention which fall within the true spirit and scope of the invention.

I claim:

1. A vision training device for a sports player comprising:
   a. sensor means for generating a timing signal when the trajectory of a ball commences from a predetermined release area;
   b. timing means coupled to said sensor means for receiving the timing signal and for generating a delayed output signal at a predetermined time interval after the timing signal is received; and
   c. means coupled to said timing means and positioned in the player's line of vision between the player and the location of the ball release area for interrupting the player's view of the ball when said timing means generates the delayed output signal, whereby the player can observe the trajectory of the ball for only a predetermined distance after it is released.

2. The vision training device of claim 1 wherein said sensor means includes a pressure actuated switch.

3. The vision training device of claim 1 wherein said timing means includes an electronic timer.

4. The vision training device of claim 3 wherein said electronic timer is coupled to said sensor means by first pair of wires and to said interrupting means by second set of wires.

5. The vision training device of claim 1 wherein said interrupting means is coupled to the player's head.

6. The vision training device of claim 5 wherein said interrupting means includes:
   a. a mask positioned in front of the player's face and including an aperture aligned with the player's eyes; and
   b. means for covering said aperture when said timing means generates the delayed output signal.

7. The vision training device of claim 6 wherein said covering means includes:
   a. a visor; and
   b. means for displacing said visor over the aperture in said mask in response to the delayed output signal from said timing means.

8. The vision training device of claim 7 wherein said displacing means includes:
   a. a hinge having a first end coupled to said mask in proximity to the aperture in said mask and a second end coupled to said visor to permit said visor to be displaced into a first position out of the player's line of vision and into a second position in which the player's view of the ball is interrupted;
   b. means for biasing said visor into the second position; and
   c. means for locking said visor in the first position and for releasing said visor upon receipt of the delayed output signal from said timing means to permit said biasing means to displace said visor into the second position.

9. The vision training device of claim 8 wherein said biasing means includes a spring.

10. The vision training device of claim 9 wherein said spring is coupled to said hinge.

11. The vision training device of claim 8 wherein said locking means includes a solenoid-actuated latch.

12. The vision training device of claim 11 wherein said solenoid-actuated latch includes:
    a. a latch coupled to said mask and displaceable between first and second positions;
    b. a solenoid coupled to said latch for displacing said latch between the first and second positions; and
    c. a holding clip coupled to said visor for engaging said latch when said latch is in the first position and for releasing said visor when said latch is in the second position.

13. A vision training device for a baseball batter comprising:
    a. a pressure actuated switch for generating a timing signal when the lead foot of a baseball pitcher contacts said switch as the pitcher releases a ball;
    b. timing means coupled to said pressure actuated switch for generating a delayed output signal at a predetermined time interval after the pitcher's foot contacts said pressure switch; and
    c. means coupled to said timing means and positioned in the batter's line of vision between the batter and the position where the pitcher releases the ball for interrupting the batter's view of the ball when said timing means generates the delayed output signal, whereby the batter can observe the trajectory of the ball for only a predetermined distance after it is released from the hand of the pitcher.

14. The vision training device of claim 13 wherein said interrupting means includes:
   a. a mask positioned in front of the batter's face and including an aperture aligned with the batter's eyes; and
   b. means for covering said aperture when said timing means generates the delayed output signal.

15. The vision training device of claim 14 wherein said covering means includes:
   a. a visor; and
   b. means for displacing said visor over the aperture in said mask in response to the delayed output signal from said timing means.

16. The vision training device of claim 15 wherein said displacing means includes:
   a. a hinge having a first end coupled to said mask in proximity to the aperture in said mask and a second end coupled to said visor to permit said visor to be displaced into a first position out of the batter's line of vision and into a second position in which the batter's view of the ball is interrupted;
   b. means for biasing said visor into the second position; and
   c. means for locking said visor in the first position and for releasing said visor upon receipt of the delayed output signal from said timing means to permit said biasing means to displace said visor into the second position.

17. The vision training device of claim 16 wherein said locking means includes:
   a. a latch coupled to said mask and displaceable between first and second positions;
   b. a solenoid coupled to said latch for displacing said latch between the first and second positions; and
   c. a holding clip coupled to said visor for engaging said latch when said latch is in the first position and for releasing said visor when said latch is in second position.

18. The vision training device of claim 16 wherein said biasing means includes a spring coupled to said hinge.

* * * * *